United States Patent [19]

Craveri et al.

[11] 3,997,397
[45] Dec. 14, 1976

[54] PRODUCTION OF PROTEIC MATERIALS FROM YEAST CELLS

[75] Inventors: Renato Craveri; Cesarina Colla; Valeria Cavazzoni, all of Milan, Italy

[73] Assignee: Societa Italiana Resine S.I.R. S.p.A., Milan, Italy

[22] Filed: Apr. 9, 1975

[21] Appl. No.: 566,474

[30] Foreign Application Priority Data

Apr. 19, 1974 Italy .................................. 21650/74

[52] U.S. Cl. ..................................... 195/5; 426/60; 260/112 R
[51] Int. Cl.$^2$ ........................ C12B 1/00; A23J 1/18
[58] Field of Search ............... 195/4, 52, 28 R, 29, 195/37, 66 R, 67, 72, 82, 83, 90, 96, 49, 65; 426/60; 260/112 R

[56] References Cited

UNITED STATES PATENTS

| | | | |
|---|---|---|---|
| 3,193,390 | 7/1965 | Champagnat et al. | 195/82 X |
| 3,330,738 | 7/1967 | Napier | 195/5 X |
| 3,716,452 | 2/1973 | Kitamura et al. | 195/65 X |
| 3,865,691 | 2/1975 | Ridgway et al. | 195/82 X |

*Primary Examiner*—R. B. Penland
*Attorney, Agent, or Firm*—Sughrue, Rothwell, Mion, Zinn & Macpeak

[57] ABSTRACT

Proteic material is produced from yeast cells without prior treatment of the cells by subjecting them to lysis action by means of an enzyme complex obtained from strains of the genus Cytophaga.

8 Claims, No Drawings

PRODUCTION OF PROTEIC MATERIALS FROM YEAST CELLS

This invention concerns the production of proteic materials from yeast cells and more particularly to a process for producing lysates from live yeast cells by means of enzymatic preparations of microbic origin.

A familiar problem is the world shortage of proteic material for use as foodstuff, and more specifically of protein of high biological value.

This problem has given use to research into nonconventional sources of protein from yeast cells cultured on low cost substrata, such as, for example, by-products, industrial waste or discharge, as well as petrochemical derivatives. Typical examples of substrata so used are molasses, paper mill effluent, hydrolates of wood, paraffins, other hydrocarbons and the aliphatic alcohol substrata.

However, micro-organism cells so produced in bulk, especially if used in the unprocessed state, are not wholly satisfactory as food for animal or human consumption, in spite of their high protein content, due mainly to the poor digestibility of the cell walls.

In order to avoid this disadvantage there has also been developed lysis processes for yeast cells on a commercial scale.

Among the methods commonly used for effecting extraction of the cytoplasm from the inside of cells of micro-organisms are hydrolysis, plasmolysis and autolysis. These processes, however, possess disadvantages. For example, chemical hydrolysis effected by suspending cells of the micro-organism in a strongly acid or strongly alkaline aqueous solution leads to considerable loss of useful material because of degradation and denaturing of biological substances by the acid or the alkali.

Plasmolysis is effected by suspending the cells of the micro-organism in an aqueous solution containing a high concentration of inorganic saline substances or organic substances, such as, for example, sugars. This induces a change in the osmotic properties of the cellular membrane, and results in escape of the cytoplasm from within the cell. The disadvantage of this is that such escape occurs with rather low efficiency. A further disadvantage is that separation of the useful substances from the aqueous phase is rendered difficult by the presence of inorganic salts or of high concentrates of organic compounds.

Autolysis is effected by suspending the cells of the micro-organism in water, adjusting the suspension to a certain pH and warming for many hours, or by the addition of organic solvents. In this way the integrity of the cellular surface is broken down by the action of enzymes contained within the cell. However, such a process also has the disadvantage that this phenomenon does not occur in all the cells present, and anyway the lysis is not sufficiently extensive to allow total escape of the intracellular substances.

An improved process has now been found for producing lysates from yeast biomasses which makes it possible to eliminate the disadvantages possessed by the known lysis processes described above.

According to the method of the present invention, proteic material is produced by means of a heterolysis of live yeast cells by contact with an enzymatic complex which is economically produced from another micro-organism, more precisely, from bacteria of the Cytophaga type.

Preferably the lysis process is carried out in a fermenter by adding a cellular suspension of live yeast cells to a lysis-producing culture filtrate and operating at optimal temperatures of 40°–45° C under gentle, preferably rotary, agitation, for periods of the order of 2–4 hours.

The live yeasts which are to be subjected to lysis may be of various kinds, but preferably those of the type *Candida lipolytica, Candida vini, Candida utilis, Hanseniaspora valbyensis, Kloeckera apiculata, Kloeckera africana, Kloeckera* sp. and *Saccharomycodes ludwigii*. The said yeasts may be cultured on several different substrata such as, for example, paraffins, molasses or aliphatic alcohols.

According to one preferred form of the process of this invention, live cells of the same yeasts as are to be subjected to lysis are used as culturing ingredients for growing the Cytophaga producing the lytic factor.

For this purpose, for growing a submerged culture of Cytophaga, a culture soil is preferably used containing from 0.5 to 2% as dry matter of live yeast and from 0.1 to 0.5% by weight of autoclavate yeast, these yeasts being, as already stated, of the same type as those which are to be subjected to lysis.

According to this invention the cultural filtrate of the strains of Cytophaga containing the active enzymatic complex is used in the lysis, without any previous concentration, or extraction, or drying of the said active complex.

It is known that lytic enzymes capable of acting upon the cells or cell walls of yeasts are produced from various groups of micro-organisms. The enzymatic complexes produced from the said micro-organisms will, however, be active only upon cells which have been treated under heat, dried either with acetone or lyophilizated (freeze-dried) or subjected to chemical pretreatment, for example, with thiols. The enzymatic complexes act only with great difficulty upon non-pretreated live cells.

Processes have now been devised for cultivation of strains of Cytophaga for producing lytic complexes which are capable of providing proteic lysates from biomasses of live yeast without any pretreatment of the yeasts.

Operational methods have also been found for achieving enzymatic lysis of such live cells, without any pretreatment, from various species of yeasts, even in a static stage of their development. As has already been said, these yeasts can be obtained in various ways such as, for example, in the fermentation of molasses, paraffins or aliphatic alcohols.

Another advantage of the invention is the direct use of the filtrate of the culture of the strains of Cytophaga containing the active enzymatic complex, without having to use costly methods of concentration or extraction or drying of the active complex.

Another advantage of the invention is that the enzymatic complex, produced in a submerged culture, allows the production of proteic lysates of interest to industry from biomasses of various yeasts.

It should be noted in this connection that the best yeasts, for food purposes, are those in which the protein is well balanced in its various amino acids and conforms as closely as possible to the biological value standard which is laid down, for example, by the FAO.

A further advantage of the enzymatic lysis process of this invention is that it allows not only almost total recovery of the proteic cytoplasmatic content, made available by lysis of the cell wall, but also recovery of various elements of the said wall of potential food value. The cell walls of yeasts consist, as is known, principally of proteins and sugar polymers. This advantage is noticeable in that the cell walls of the yeasts may represent up to 30% by weight of the cell mass.

Moreover the enzymatic treatment is not carried out at high temperature, thus safeguarding the vitamin constituents of the yeast cells, which would otherwise be degraded, as happens when the cells walls are attacked by methods such as chemical hydrolysis already referred to or drastic heat treatments.

Other characteristics and advantages of the invention will become evident in the course of the following detailed description of a process in accordance with the invention.

The process of this invention is based on effective enzymatic heterolysis of biomasses of live yeasts by means of enzymatic complexes produced from microbic strains selected from the Cytophaga genus.

In order to obtain this result the following procedure was used.

a. The Cytophaga strains being used are kept by transplanting them every 10–15 days, upon SL soil and incubating them at 26°–30° C for 36–48 hours, then keeping them at 4°–8° C. The SL soil consists of the Stanier mineral solution ($K_2HPO_4$ 1g, $MgSO_4$ 0.5g, NaCl 0.5g, $FeCl_3$ traces, $CaCl_2$ 0.1g, to 1000ml of distilled $H_2O$, pH 7–7.2), agarized to 15% and added to 6% of dried yeast cells.

The said soil may be prepared after having melted the agar in the water bath there are added for each liter of soil 50ml of a suspension containing 15%, as dry matter, of cells of fresh bakers' yeast, sterilization then being effected at 115° C for 20 minutes.

A culture soil (LL) which is simple and suitable for the production of a lytic complex in submerged culture consists, as dry matter content, of 0.2.% of yeast autoclaved at 110° C for 20 minutes, plus 1.2% of live yeast, in sterile spring water.

For the production of an enzymatic complex in a submerged culture there were used, for the inoculum preparation, 750ml flasks with 100ml of cultural soil LL.

Each flask was inoculated with 6ml of a suspension of the Cytophaga strain, with a turbidity equal to 33% of the transmittance, obtained from cultures of around 40 hours. The flasks were subjected to reciprocating agitation (6cm. stroke, 120 cycles per min) and maintained thermostatically at 28°–30° C.

After 24–36 hours of fermentation these liquid culture broths were used as inocula for the production of the lytic complex in fermenters.

For this purpose there were used 20 lt fermenters with 10 l of LL soil, under the following conditions: inoculum 5–10%, agitation 100–200 cycles per minute, aeration 0.5 volumes of air per volume of soil per minute, time of fermentation 30–45 hours, temperature 28°–30° C.

b. When production of the enzymatic complex has been achieved in the fermenter, the lysis process is prepared by addition of the culture filtrate obtained by centrifuging the fermentation culture broth of the Cytophaga to the yeast biomass in a second fermenter. One process used has the following conditions: to one volume of lytic cultural filtrate there is added an equal volume of the cellular suspension at 14%, as dry matter, of live yeast to be subjected to lysis; temperature 40°–45° C; rotary agitation at 50 r.p.m. period of treatment 2–3 hours.

At the end of this treatment the biomasses will have been lysated with a yield above 90% in the four cases recorded below.

The micro-organism strain of the Cytophaga used by us at present was selected by successive isolations from the soil. It was lodged at the Institute of Industrial Micro-biology, at the Milan University of Study, with the seal 21B. The taxonomic study followed the guidance of: Roberts, S., Breed R. S., Murray Nathan Smith E.G.D. ("Bergey's Manual of Determinative Bacteriology," The Williams and Wilkins Co., Baltimore, 1957); Stanier R. (Journal of Bacteriology, vol. 53, 297–315, 1947); Salton M. R. (The Journal of General Microbiology, vol. 12, 25–30, 1955); Lewin R. A. (the Journal of General Microbiology, vol. 58, 189–206, 1969). The characteristics of the strain of Cytophaga used are described in the following paragraph.

Gram-negative rods, aerobes, non-sporeforming and heterotrophic, of variable dimensions (0.2–0.5 × 1.5–10 micron) with optimal developing temperature between 25° and 30° C. Cultural patina in translucid agar, weakly yellow pigmented, uniformly diffused and mucous especially in sugar-rich soil cultures. Good growth in nutrient-agar and agar cells (e.g. SL, see above). In nutrient-broth and SL-broth a surface film forms. Negative reduction of nitrates; positive hydrolysis of the amide; positive formation of catalase; positive hydrolysis of casein; weakly positive liquification of gelatine; positive coagulation of milk. This strain has shown itself to possess lytic activity not only on cells of numerous species of autoclaved yeasts, but also on live yeast cells. It is already known from the literature that cells pretreated by heat or with chemical substances such as thiols can be submitted to lysis. Such lytic activity upon live cells was not reported.

For the production of the enzyme complex a culture soil has been adopted which is of simple and economical composition with a base of the same yeast cells as are to be subjected to lysis (e.g., 1.2% live cells and 0.2% pretreated cells, in spring water).

It should be noted that the best results are obtained with this kind of broth-culture, even if the strain described, or other strains of Cytophaga, can be cultivated on different culture soils.

As regards the enzymatic lysis of live yeasts the best results were obtained with the following yeasts: Candida utilis, Candida vini, Candida lipolytica, Hanseniaspora valbyensis, Kloeckera apiculata, Kloeckera africana, Kloeckera sp., Saccharomylodes ludwigii. Analysis of the total chemical and amino acid composition of the cellular lysate, and comparatively of the initial biomass, has given optimal results. The procedure used can lead to an almost total proteic recovery whilst on the other hand the quantity of fibre in the lysates is shown to be less (see Table 1) than in the initial biomass.

The cellular substances are then moreover found in the lysates in a more readily available form, owing to lysis of the walls which has taken place.

Table 1

Chemical composition of an initial yeast biomass from paraffin and of its lysate; g/100 g dry matter

| Component | Initial biomass | Lysate | Lysate/100g. init. biomass | Individual recoveries % |
|---|---|---|---|---|
| Protein | | | | |

Table 1-continued

Chemical composition of an initial yeast biomass from paraffin and of its lysate; g/100 g dry matter

| Component | Initial biomass | Lysate | Lysate/100g. init. biomass | Individual recoveries % |
|---|---|---|---|---|
| NX 6.25 | 45.2 | 46.9 | 44.8 | 99.1 |
| Lipoids | 14.2 | 13.6 | 13.0 | 91.5 |
| Ashes | 7.0 | 4.8 | 4.6 | 41.4 |
| Fibre | 0.8 | 0.2 | 0.19 | 23.7 |
| Non-azotized extractives (per difference) | 32.8 | 34.5 | 32.9 | |

Differences in the plan of the aminoacids are slight (see Table 2).

Table 2

Aminoacid composition of the initial yeast biomass from paraffin and of its lysate; g/100 g dry matter

| Aminoacids | Initial biomass | Lysate |
|---|---|---|
| Asparagine | 3.96 | 3.55 |
| Threonine | 1.76 | 2.23 |
| Serine | 2.26 | 1.89 |
| Glutam ac. | 5.15 | 4.55 |
| Glycine | 1.81 | 1.86 |
| Alanine | 2.50 | 2.24 |
| Valine | 1.93 | 2.34 |
| Methionine | 0.74 | 0.62 |
| Isoleucine | 1.65 | 1.99 |
| Leucine | 3.06 | 3.12 |
| Tyrosine | 1.21 | 1.58 |
| Phenylalanine | 1.62 | 1.82 |
| Proline | 2.12 | 2.30 |
| Cisteic ac | 1.30 | 0.94 |
| Lysine | 3.75 | 2.28 |
| Histidine | 0.98 | 0.90 |
| Arginine | 2.48 | 1.72 |
| Tryptophan | 0.50 | 0.62 |
| TOTALS | 38.78 | 36.55 |

By way of example, without restricting the generality of the present invention, there will be described hereinbelow a few processes for preparation of the enzymatic complexes and a subsequent lysis process of yeast biomasses.

EXAMPLE 1 a. Preparation of the enzymatic complex.

The following procedure was used; preparation of a suspension of Cytophaga cells, strain 21b II, slant-incubated for 48 hours and inoculated in a flask with 50ml of LL soil in which the yeast is represented by Candida lipolytica; the suspension is kept under agitation at 28° C for 24 hours; inoculum 10% in 20 liter fermenter with 10 liters of soil. Fermentation conditions were as follows: temperature 28° C, agitation 150 r.p.m. aeration 0.5 volumes of air per volume of culture soil per minute, time of incubation 30–35 hours. One obtains a broth culture at pH around 8, with a marked lytic activity upon the live cells of a number of yeasts.

The optimal temperatures of lysis activity of culture filtrate upon live cells is about 40°–45° C.

On the basis of the tests made, the use of buffers will not prove necessary.

b. Lysis process of a yeast biomass.

Having produced the enzymatic complex in a fermenter the lysis process was carried out, adding the culture filtrate to a biomass of live yeast of Candida lipolytica obtained from fermentation in paraffin substrates.

The culture filtrate was added to the yeast biomass in a second fermenter, by the following procedure: to one volume of lytic culture filtrate there is added an equal volume of the cellular suspension of yeast at 14% of dry matter: temperaure 43° C, agitation 50 revolutions per minute, time 3 hours.

At the end of the treatment the biomass will be lysated with a yield of 95%, which corresponds to the use of about seven liters of lytic broth in order to lysate about 1Kg., as dry matter, of biomass in a period of three hours.

Referring to the whole quantity of yeast used in the process for production of the enzymatic filtrate and for the production of the lysate, the absolute yield of the whole process is about 89%. The proteic lysate obtained by the said process can be concentrated by various procedures, such as for example, partial or total evaporation of the aqueous phase under vacuum, spray drying or lyophilization.

EXAMPLE 2 a. Preparation of the enzymatic complex.

A suspension of Cytophaga cells was prepared, strain 21b II, slant-incubated for 48 hours, was inoculated in a flask of 500 ml with 50 ml of LL soil in which the yeast is Candida vini. The suspension is kept under agitation at 28° C for 24 hours; inoculum 10% in a 20 liter fermenter with 10 liters of soil. The fermentation conditions were the following: temperature 28° C, agitation 150 revolutions per minute, aeration 0.5 volumes of air per volume of culture soil per minute, time of incubation 24–30 hours. A culture broth is obtained at pH about 8, with marked lytic activity upon live cells of numerous yeasts. The optimal temperature of lytic activity of the culture filtrate upon live cells is about 40°–45° C. Based on the tests which have been made, the use of buffers will not prove necessary.

b. Lysis process of biomass of yeast.

When the enzymatic complex has been produced in a fermenter, the lysis process is carried out, adding the culture filtrate to a biomass of live yeast of Candida vini resulting from a fermentation in which ethanol is used as a source of carbon and energy.

The culture filtrate is added to the yeast biomass in a second fermenter, with the following procedure: to one measure of lytic culture filtrate there is added an equal measure of the cellular suspension of yeast at 14% of dry matter; temperature 43° C, agitation 50 revolutions per minute, time about 2 hours. At the end of the treatment the biomass will be lysated with a yield greater than 95%. With reference to the total quantity of yeast used in the process for production of the enzymatic filtrate and for the production of the lysate the absolute yield of the whole process is at about 90%.

The proteic lysate obtained by the aforesaid procedure may be concentrated by different methods, such as, for example, partial or total evaporation of the aqueous phase under vacuum, spray drying or lyophylisation.

EXAMPLE 3 a. Preparation of the enzymatic complex.

A suspension of Cytophaga cells, strain 21b II, slant-incubated for 48 hours, was prepared and this was inoculated in a 500 ml flask with 50ml of LL soil in which the yeast is Candida utilis. The suspension is kept in agitation at 28° C for 24 hours; inoculum 10% in a 20 liter fermenter with 10 liters of soil. Fermentation conditions were as follows: temperature 28° C, agitation 150 revolutions per minute, aeration 0.5 measures of air per measure of culture soil per minute, time of incubation 30–36 hours. A culture broth is obtained at pH about 8, with marked lytic activity upon live cells of numerous yeasts. The optimal temperature of lytic activity of the culture filtrate upon live cells is at about 40°–45° C. On the basis of the tests made, the use of buffers does not prove necessary.

b. Lysis process of yeast biomass.

Having obtained production of the enzymatic complex in the fermenter, the lysis process was carried out by adding the culture filtrate to a biomass of live yeast of Candida utilis resulting from fermentation in sugar substrates such as molasses of beet or cane.

The culture filtrate was added to the biomass of yeast in a second fermenter, with the following procedure: to one measure of lytic culture filtrate there is added an equal measure of the cellular suspension of yeast at 14% of dry matter; temperature 45° C, agitation 50 revolutions per minute, time about 3 hours. At the end of the treatment the biomass will be lysated with a yield of about 90%. As to the total quantity of yeast used in the production of the enzymatic filtrate and of the lysate, the absolute yield of the whole process is about 85%.

The proteic lysate obtained by the said procedure can be concentrated by various procedures, such as for example, partial or total evaporation of the aqueous phase under vacuum, spray drying or lyophylisation.

EXAMPLE 4 a. Preparation of the enzymatic complex.

A suspension of Cytophaga cells, strain 21b II, slant-incubated for 48 hours, was prepared and this was inoculated in a 500 ml flask with 50 ml of LL soil in which the yeast is Kloeckera sp. The suspension is kept in agitation at 28° C for 24 hours; inoculum 10% in 20 liter fermenter with 10 liters of soil. The fermentation conditions were the following: temperatures 28° C, agitation 150 revolutions per minute, aeration 0.5 measures of air per measure of culture soil per minute, incubation time about 40 hours. A culture broth is obtained at pH about 8, with marked lytic activity on live cells of numerous yeasts. The optimal temperature of lytic activity of the culture filtrate on live cells is about 40°–45° C. On the basis of the tests effected, the use of buffers will not be necessary.

b. Lysis process of a yeast biomass.

Having produced the enzymatic complex in the fermenter, the lysis process was carried out by adding the culture filtrate to a biomass of live yeast of Kloeckera sp. derived from fermentation in which methanol is used as a source of carbon and of energy.

The culture filtrate was added to the yeast biomass in a second fermenter, by the following method: to one measure of lytic culture filtrate there is added an equal measure of the cellular suspension of yeast at 14% of dry matter temperature 45° C, agitation 50 revolutions per minute, time about 4 hours. At the end of the treatment the biomass will be lysated with a yield of about 85%. As regards the total quantity of yeast used in the process for production of the enzymatic filtrate and for the production of the lysate the absolute yield of the whole process is about 80%.

The proteic lysate obtained by the process can be concentrated by various methods, such as for example, partial or total evaporation of the aqueous phase under vacuum, spray drying or lyophilisation.

What is claimed is:

1. A process for producing proteic material from live yeast cells selected from the group consisting of *Candida lipolytica*, *Candida vini*, *Candida utilis*, *Hanseniaspora valbyensis*, *Kloeckera apiculata*, *Kloeckera africana*, *Kloeckera* sp., and *Saccharomycodes ludwigii* comprising (1) preparing a culture filtrate for use as a lytic factor for said yeast cells by growing a submerged culture of bacteria of the genus Cytophaga on a culture soil comprising live cells of yeast of the same species as that to be subsequently subject to lysis and (2) then utilizing directly the resulting culture filtrate as a lytic factor for the lysis of biomasses of said live yeasts, without subjecting said live yeast to any pretreatment.

2. The process defined in claim 1, wherein the lysis process is carried out in a fermenter by adding to a lysis-producing culture filtrate a suspension of live yeast cells at temperatures from 40° to 45° C under rotary agitation for a processing time of 2–4 hours.

3. The process defined in claim 1, wherein the yeasts employed are obtained by culturing on a paraffin substrate.

4. The process defined in claim 1, wherein the yeasts employed are obtained by culturing on a molasses substrate.

5. The process defined in claim 1, wherein the yeasts employed are obtained by culturing on an aliphatic alcohol substrate.

6. The process defined in claim 1, wherein, for growing a submerged culture of the Cytophaga producing the lytic factor, of live yeast and from 0.1 to 0.5%, as dry matter, of autoclavate yeast, these yeasts being of the same species as those which will subsequently be subjected to lysis.

7. The process of claim 1 consisting essentially of said process steps.

8. The process of claim 1 wherein said bacteria of the genus Cytophaga is the strain 21B II lodged at the Institute of Industrial Micro-Biology at the Milan University of Study.

* * * * *